United States Patent
Perron et al.

(10) Patent No.: US 10,894,820 B2
(45) Date of Patent: Jan. 19, 2021

(54) ANTIRETROVIRAL DRUG TARGETING HUMAN ENDOGENOUS RETROVIRUS

(71) Applicant: Geneuro SA, Plan-les-Ouates (CH)

(72) Inventors: Herve Perron, Saint Genis les Ollieres (FR); Francois Curtin, Chambesy (CH); Alois Lang, Bern (CH); Raphael Faucard, Mont-Saxonnex (FR); Julie Medina, Lentilly (FR); Alexandra Madeira, Mont-Saxonnex (FR); Nadege Gehin, Saint-Sylvestre (FR)

(73) Assignee: GENEURO SA, Plan-les-Ouates (CH)

( * ) Notice: Subject to any disclaimer, the term of this patent is extended or adjusted under 35 U.S.C. 154(b) by 0 days.

(21) Appl. No.: 16/362,193

(22) Filed: Mar. 22, 2019

(65) Prior Publication Data

US 2019/0263895 A1 Aug. 29, 2019

Related U.S. Application Data

(63) Continuation of application No. 15/314,017, filed as application No. PCT/EP2015/061691 on May 27, 2015, now abandoned.

(30) Foreign Application Priority Data

May 28, 2014 (EP) .................................. 14305806

(51) Int. Cl.
| | | |
|---|---|---|
| *C07K 16/10* | (2006.01) | |
| *A61K 39/42* | (2006.01) | |
| *A61K 45/06* | (2006.01) | |
| *A61K 31/7072* | (2006.01) | |
| *C12Q 1/70* | (2006.01) | |
| *A61K 39/00* | (2006.01) | |

(52) U.S. Cl.
CPC ...... *C07K 16/1063* (2013.01); *A61K 31/7072* (2013.01); *A61K 39/42* (2013.01); *A61K 45/06* (2013.01); *C07K 16/1036* (2013.01); *C12Q 1/702* (2013.01); *A61K 2039/505* (2013.01); *A61K 2039/54* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/76* (2013.01); *C12N 2740/10011* (2013.01)

(58) Field of Classification Search
CPC .......... C07K 16/1036; C07K 2317/565; A61K 31/7072; A61K 39/42; C12N 2740/10011
See application file for complete search history.

(56) References Cited

U.S. PATENT DOCUMENTS

| | | | | |
|---|---|---|---|---|
| 8,715,656 B2 * | 5/2014 | Bernard | ............. | C07K 16/1036 424/130.1 |
| 9,550,824 B2 * | 1/2017 | Bernard | ............. | C07K 16/1036 |
| 9,815,888 B2 * | 11/2017 | Bernard | ............. | C07K 16/1036 |
| 2006/0088820 A1 | 4/2006 | Perron et al. | | |
| 2012/0321637 A1 * | 12/2012 | Dong | ................. | A61K 31/4025 424/142.1 |

FOREIGN PATENT DOCUMENTS

| | | |
|---|---|---|
| CN | 102143975 A | 8/2011 |
| FR | 2 865 403 A1 | 7/2005 |
| FR | 2 912 314 A1 | 8/2008 |
| JP | 2002-539804 A | 11/2002 |
| JP | 2011-527887 A | 11/2011 |
| WO | 2003/027247 A2 | 4/2003 |
| WO | 2010/003977 A1 | 1/2010 |
| WO | 2014/053489 A1 | 4/2014 |

OTHER PUBLICATIONS

Voisset, C., et al., 2000, Chromosomal distribution and coding capcity of the human endogenous retrovirus HERV-W family, AIDS Res. Human Retrovir. 16(8):731-740.*
Xiang, J., et al., 1999, Light-chain framework region residue Tyr71 of chimeric B72.3 antibody plays an important role in influencing the TAG72 antigen binding, Prot. Engineering 12(5):417-421.*
Winkler, K., et al., 2000, Changing the antigen binding specificity by single point mutations of an anti-p24 (HIV-1) antibody, J. Immunol. 165:4505-4514.*
Sela-Culang, I., et al., 2013, The structural basis of antibody-antigen recognition, Front. Immunol. 4:article 302, pp. 1-13.*
Curtin, F., et al., 2012, GNbAC1, a humanized monoclonal antibody against the envelope protein of multiple sclerosis-associated endogenous retrovirus: A first-in-humans randomized clinical study, Clin. Therap. 34(12):2268-2278.*
Christensen: "HERVs in Neuropathogenesis", Journal of Neuroimmune Pharmacology, vol. 5, No. 3, pp. 326-335, Apr. 27, 2010.
Derfuss et al: "A phase IIa randomised clinical study of GNbAC1, a humanised monoclonal antibody against the envelope protein of multiple sclerosis-associated andogenous retrovirus in multiple sclerosis patients", Multiple Sclerosis, vol. 21, No. 7, pp. 885-893, May 20, 2015.

* cited by examiner

*Primary Examiner* — Jeffrey S Parkin
(74) *Attorney, Agent, or Firm* — W&C IP

(57) ABSTRACT

The invention relates to an antibody, a fragment or a derivative thereof, for use as an antiretroviral drug targeting a virus belonging to human endogenous retroviruses type W (HERV-W), wherein said antibody, fragment or derivative thereof is directed against HERV-W Envelope protein (HERV-W Env). The invention also relates to a composition comprising said antibody and a retroviral reverse-transcriptase inhibitory drug, for use as an antiretroviral drug targeting a virus belonging to HERV-W.

18 Claims, 5 Drawing Sheets

Figure 1A:
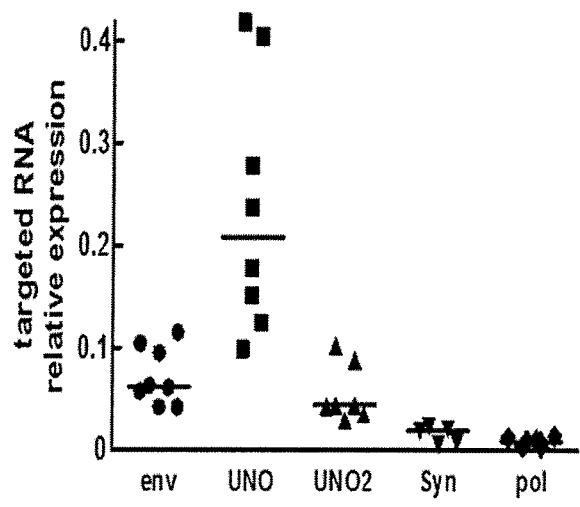

Specification includes a Sequence Listing.

SEQUENCE LISTING

```
<160> NUMBER OF SEQ ID NOS: 28

<210> SEQ ID NO 1
<211> LENGTH: 10
<212> TYPE: PRT
<213> ORGANISM: Mus musculus

<400> SEQUENCE: 1

Ser Ala Ser Ser Ser Val Ser Tyr Met Tyr
1               5                   10

<210> SEQ ID NO 2
<211> LENGTH: 7
<212> TYPE: PRT
<213> ORGANISM: Mus musculus

<400> SEQUENCE: 2

Arg Thr Ser Asn Leu Ala Ser
1               5

<210> SEQ ID NO 3
<211> LENGTH: 9
<212> TYPE: PRT
<213> ORGANISM: Mus musculus

<400> SEQUENCE: 3
```

```
Gln Gln Tyr Gln Ser Leu Pro Leu Thr
1               5

<210> SEQ ID NO 4
<211> LENGTH: 5
<212> TYPE: PRT
<213> ORGANISM: Mus musculus

<400> SEQUENCE: 4

Asp Tyr Glu Met His
1               5

<210> SEQ ID NO 5
<211> LENGTH: 17
<212> TYPE: PRT
<213> ORGANISM: Mus musculus

<400> SEQUENCE: 5

Ala Val Ala Pro Glu Thr Gly Gly Thr Ala Tyr Asn Gln Lys Phe Lys
1               5                   10                  15

Gly

<210> SEQ ID NO 6
<211> LENGTH: 7
<212> TYPE: PRT
<213> ORGANISM: Mus musculus

<400> SEQUENCE: 6

Thr Val Val Pro Phe Ala Tyr
1               5

<210> SEQ ID NO 7
<211> LENGTH: 106
<212> TYPE: PRT
<213> ORGANISM: Artificial Sequence
<220> FEATURE:
<223> OTHER INFORMATION: Synthetic VL

<400> SEQUENCE: 7

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Tyr Trp Tyr Gln Gln Lys Pro Gly Lys Ala Pro Lys Ala Trp Ile Tyr
            35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr Gln Ser Leu Pro Leu Thr
                85                  90                  95

Phe Gly Gly Gly Thr Lys Val Glu Ile Lys
            100                 105

<210> SEQ ID NO 8
<211> LENGTH: 116
<212> TYPE: PRT
<213> ORGANISM: Artificial Sequence
<220> FEATURE:
<223> OTHER INFORMATION: Synthetic VH

<400> SEQUENCE: 8
```

```
Gln Val Gln Leu Val Gln Ser Gly Ala Glu Val Lys Lys Pro Gly Ser
 1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Val Ala Pro Glu Thr Gly Gly Thr Ala Tyr Asn Gln Lys Phe
50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Val Val Pro Phe Ala Tyr Trp Gly Gln Gly Thr Leu Val
            100                 105                 110

Thr Val Ser Ser
            115

<210> SEQ ID NO 9
<211> LENGTH: 443
<212> TYPE: PRT
<213> ORGANISM: Artificial Sequence
<220> FEATURE:
<223> OTHER INFORMATION: Synthetic HC

<400> SEQUENCE: 9

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Val Ala Pro Glu Thr Gly Gly Thr Ala Tyr Asn Gln Lys Phe
50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Val Val Pro Phe Ala Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240
```

-continued

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 10
<211> LENGTH: 213
<212> TYPE: PRT
<213> ORGANISM: Artificial Sequence
<220> FEATURE:
<223> OTHER INFORMATION: Synthetic LC

<400> SEQUENCE: 10

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Lys Ala Pro Lys Ala Trp Ile Tyr
            35                  40                  45

Arg Thr Ser Asn Leu Ala Ser Gly Val Pro Ser Arg Phe Ser Gly Ser
50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr Gln Ser Leu Pro Leu Thr
            85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

-continued

```
Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
cttccagaat tgaagctgta aagc                                              24

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
gggttgtgca gttgagattt cc                                                22

<210> SEQ ID NO 13
<211> LENGTH: 26
<212> TYPE: DNA
<213> ORGANISM: Artificial Sequence
<220> FEATURE:
<223> OTHER INFORMATION: Synthetic PROBE / FAM in 5' position and TAMRA
      in 3' position

<400> SEQUENCE: 13
ttcttcaaat ggagccccag atgcag                                            26

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
actttgtctc ttccagaatc                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
gcggtagatc ttagtcttgg                                                   20

<210> SEQ ID NO 16
<211> LENGTH: 17
<212> TYPE: DNA
<213> ORGANISM: Artificial Sequence
```

```
<220> FEATURE:
<223> OTHER INFORMATION: Synthetic PROBE / FAM in position 5' and TAMRA
      in position 3'

<400> SEQUENCE: 16
atggagccca agatgca                                                    17

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
ggcggttagc aagtctaaag                                                 20

<210> SEQ ID NO 18
<211> LENGTH: 21
<212> TYPE: DNA
<213> ORGANISM: Artificial Sequence
<220> FEATURE:
<223> OTHER INFORMATION: Synthetic Primer

<400> SEQUENCE: 18
atggaacagg tcactgactc c                                               21

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
gtatgtctga tgggggtgga g                                               21

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

<400> SEQUENCE: 20
ctagtccttt gtaggggcta gag                                             23

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
tgccccatcg tataggagtc t                                               21

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
catgtacccg ggtgagttgg                                                 20
```

```
<210> SEQ ID NO 23
<211> LENGTH: 19
<212> TYPE: DNA
<213> ORGANISM: Artificial Sequence
<220> FEATURE:
<223> OTHER INFORMATION: Synthetic primer

<400> SEQUENCE: 23
cctgtacgtc ctgactctc                                                    19

<210> SEQ ID NO 24
<211> LENGTH: 19
<212> TYPE: DNA
<213> ORGANISM: Artificial Sequence
<220> FEATURE:
<223> OTHER INFORMATION: Synthetic primer

<400> SEQUENCE: 24
cttgggctaa tgcctggcc                                                    19

<210> SEQ ID NO 25
<211> LENGTH: 21
<212> TYPE: DNA
<213> ORGANISM: Artificial Sequence
<220> FEATURE:
<223> OTHER INFORMATION: Synthetic PROBE/ FAM in position 5' and TAMRA
      in position 3'

<400> SEQUENCE: 25
ccaacgtctc aactcacctg g                                                 21

<210> SEQ ID NO 26
<211> LENGTH: 24
<212> TYPE: DNA
<213> ORGANISM: Artificial Sequence
<220> FEATURE:
<223> OTHER INFORMATION: Synthetic primer

<400> SEQUENCE: 26
ggtgtgaacc atgagaagta tgac                                              24

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tggcatggac tgtggtcatg                                                   20

<210> SEQ ID NO 28
<211> LENGTH: 27
<212> TYPE: DNA
<213> ORGANISM: Artificial Sequence
<220> FEATURE:
<223> OTHER INFORMATION: Synthetic PROBE / VIC in position 5' and TAMRA
      in position 3'

<400> SEQUENCE: 28
agcctcaaga tcatcagcaa tgcctcc                                           27
```

ANTIRETROVIRAL DRUG TARGETING HUMAN ENDOGENOUS RETROVIRUS

FIELD OF THE INVENTION

The present invention relates to a novel antiretroviral drug targeting human endogenous retrovirus.

BACKGROUND OF THE INVENTION

Human endogenous retroviruses (HERV) are complex and heterogeneous multicopy families of genetic elements which are remnants of ancestral retroviral infections having entered the genome of certain species through insertions within germline cells. Altogether HERV elements represent about 8% of the human genome and, when HERV elements have retained transcriptional activity they rarely cause complete retroviral genome expression and this is barely expected to arise from completely functional proviral copies.

Multiple Sclerosis associated Retrovirus element (MSRV), which is a member of type-W human endogenous retrovirus family (HERV-W), was first isolated from cells of patients suffering from multiple sclerosis. MSRV is normally latent in the genome of individuals, but when triggered by co-factors, such as certain common viruses, it can be reactivated and it can further express an envelope protein of the HERV-W family. The inventors previously investigated this mechanism and unveiled that it is a major triggering and aggravating factor in the development and progression of various diseases such as multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes such as type 1 or type 2 diabetes.

Despite possible expression of all structural retroviral genes from HERVs, i.e. of gag gene encoding matrix, capsid and nucleocapsid precursor polyprotein, together with pol gene encoding retroviral enzymes including protease, reverse-transcriptase and integrase precursor polyprotein, and together with env gene encoding the envelope precursor protein from the same HERV, no infectious retroviral copy from HERVs could be found to date.

Moreover, contrary to exogenous infectious retroviruses, HERVs are present in the DNA of all cells from each human individual and, therefore, therapeutic molecules classically used for treating human retroviruses cannot eliminate the corresponding provirus within a sub-population of reservoir cells. Many cellular and genetic constraints on these endogenous elements also make them controlled by non-retroviral molecular mechanisms, thus escaping from classical retroviral pathways. Among these various mechanisms, an involvement of gene silencing, of gene control by cellular promoter/enhancer or of genetic recombination between HERV sequences and cellular genes are known. Such features are not expected with classical exogenous retroviruses and therefore are not accessible to presently existing antiretroviral therapy.

In such conditions, treatments of classical exogenous retroviruses cannot expect to fully control pathogenic HERV expression and, consequently, to have optimal therapeutic efficiency, if any, on HERV-associated diseases.

There is thus a long time felt unfulfilled need for a novel antiretroviral therapeutic strategy targeting the HERV viruses.

SUMMARY OF THE INVENTION

The inventors have surprisingly found out that an unexpected anti-HERV effect targeting endogenous elements from the HERV-W family can reduce and inhibit HERV-W expression. Therefore, in a first aspect, the invention relates to an antibody, a fragment or a derivative thereof for use as an antiretroviral drug targeting a virus belonging to a human endogenous retrovirus (HERV), wherein said antibody is directed against HERV-W Envelope protein (HERV-W Env). Preferably, said antibody, fragment or derivative is for preventing and/or treating an HERV-W associated disease. More preferably, said antibody is for preventing and/or treating Multiple Sclerosis (MS) or Chronic Inflammatory Demyelinating Polyneuropathy (CIDP). More preferably, said antibody is a monoclonal humanized antibody, wherein the heavy chain (HC) has the amino acid sequence as set forth in SEQ ID No: 9 and the light chain (LC) has the amino acid sequence set forth in SEQ ID No: 10.

In a second aspect, the invention relates to a composition comprising, preferably consisting of, an antibody directed against HERV-W Envelope protein (HERV-W Env), a fragment or a derivative thereof and a retroviral reverse-transcriptase inhibitory drug for use as an antiretroviral drug targeting a virus belonging to human endogenous retroviruses (HERV).

In a third aspect, the invention relates to an antibody directed against HERV-W Envelope protein (HERV-W Env), a fragment or a derivative thereof and a retroviral reverse-transcriptase inhibitory drug as a combined preparation for simultaneous, separate or sequential use in a method for treating an HERV-W associated disease, preferably a disease selected from the group consisting of multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes such as type 1 or type 2 diabetes.

In a fourth aspect, the invention relates to a kit comprising at least one oligonucleotide selected from the group consisting of SEQ ID No: 11 to 28.

In a fifth aspect, the invention relates to an antibody directed against HERV-W Envelope protein (HERV-W Env), a fragment or a derivative thereof for use as an antiretroviral drug targeting a virus belonging to human endogenous retroviruses (HERV), preferably to the HERV-W family, more preferably to MSRV, in a patient suffering from an HERV-W associated disease, wherein said patient is identified by a method comprising a step i) of detecting and/or quantifying HERV-W in a biological sample.

DETAILED DESCRIPTION OF THE INVENTION

Definition

As used herein, the terms "human endogenous retrovirus" and "HERV", refer to the human endogenous retroviruses that comprise the virus belonging to the type-W endogenous retrovirus family, usually named "HERV-W".

"HERV-W" is a family of human endogenous retroviruses that was unravelled in human genome from the initial discovery of "Multiple Sclerosis associated Retrovirus", MSRV, a human retrovirus first isolated from patients with multiple sclerosis. Therefore, when studies mention "LM7" (first isolate described from MS), "MS-retrovirus", "MSRV", "Syncytin", "HERV-W 7q", "ERVW-E1", "ERVW-E2", "HERV-W copies from X chromosome" or "HERV-W", they all designate HERV-W elements.

As used herein, the term "MSRV" refers to a specific endogenous retrovirus which is a member of the HERV-W family. In the context of the present invention, the expressions "HERV-W" and "MSRV" both designate HERV-W elements. Specifically, the expressions "HERV-W Env" and "MSRV-Env" both refer to the same envelope proteins. Typically, eventual few variations in aminoacid sequence does not prevent the binding of specific anti-Env antibodies for therapeutic use, in particular an antibody having a heavy chain (HC) with the amino acid sequence as set forth in SEQ ID No: 9 and a light chain (LC) with the amino acid sequence set forth in SEQ ID No: 10.

As used herein, the expression "HERV-W associated disease" refers to a pathological condition associated with the expression of HERV-W, preferably of the HERV-W Envelope protein. Typically, said HERV-W associated disease is a chronic inflammatory disease. As used herein, the expression "chronic inflammatory disease" refers to any disease in which persisting or recurrent inflammation is driven by innate immunity and/or by adaptive immunity involved in tissue lesions and/or can be detected locally or systemically from an overexpression of pro-inflammatory molecules.

Preferably, said HERV-W associated disease is selected from the group consisting of multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes such as type 1 or type 2 diabetes. More preferably, said HERV-W associated disease is selected from the group consisting of Multiple Sclerosis (MS) and Chronic Inflammatory Demyelinating Polyneuropathy (CIDP), which both are demyelinating diseases.

As used herein, the term "treating" or "treatment", as used herein, means reversing, alleviating, inhibiting the progress of, or preventing the disorder or condition to which such term applies, or reversing, alleviating, inhibiting the progress of, or preventing one or more symptoms of the disorder or condition to which such term applies.

As used herein, the term "prevention" refers to preventing the disease or condition from occurring in a subject which has not yet presented clinical symptoms, typical lesions or physiological dysfunctions that would allow its clinical diagnosis.

As used herein, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that specifically binds an antigen. As such, the term "antibody" encompasses not only whole antibody molecules, but also antibody fragments, as well as derivatives of antibodies.

As used herein, the expression "fragment of antibody" refers to a portion of such an antibody that mimic the hypervariable region, such as a CDR (CDR-L1, CDR-L2, CDR-L3, CDR-H1, CDR-H2, CDR-H3). The fragments of antibody according to the present invention retain the binding affinity and specificity of said antibody. Such fragments are functional equivalents of said antibody and they bind at substantially the same epitope as said antibody. Examples of fragments of antibody include but are not limited to heavy chain, light chain, VL, VH, Fv, Fab, Fab', F(ab)2, and F(ab')2.

As used herein, the expression "derivative of antibody" refers to a fragment of the antibody of the invention, preferably including at least one CDR of said antibody, preferably at least one CDR3 of said antibody, fused to at least one sequence different from the natural sequence (e.g. a linker sequence of another species . . . ), said derivative having binding affinity and specificity to HERV-W Env comparable to that of the antibody of the invention. The derivatives according to the present invention retain the binding affinity and specificity of said antibody. Such derivatives are functional equivalents of said antibody and they bind at substantially the same epitope as said antibody. Examples of derivatives of antibody include, but are not limited to scFv, (scFv)2 and diabodies.

In natural antibodies, two heavy chains (HC) are linked to each other by disulfide bonds and each heavy chain is linked to a light chain (LC) by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains.

Typically, the light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine the binding site specific to the antigenic epitope. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody binding site and the antigenic epitope. Antibody binding sites are made up of residues that are primarily from the hypervariable or complementarity determining regions (CDRs). Occasionally, residues from nonhypervariable or framework regions (FR) influence the overall domain structure and hence the binding site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

As used herein, the term "chimeric antibody" refers to an antibody which comprises a VH domain and a VL domain of an antibody from any species, preferably mouse, and a CH domain and a CL domain of a human antibody.

According to the invention, the term "humanized antibody" refers to an antibody having variable region framework and constant regions from a human antibody but retains the CDRs of an antibody from any species, preferably mouse.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

As used herein, The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

As used herein, The term "Fab'" refers to an antibody fragment having a molecular weight of about 50,000 and antigen binding activity, which is obtained by cutting a disulfide bond of the hinge region of the F(ab')2.

The expressions "A single chain Fv" or "scFv"" refer to a polypeptide which is a covalently linked VH::VL heterodimer, and usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

As used herein, the expression "antibody of the invention" refers to an antibody directed against, i.e. that specifically binds to, HERV-W Envelope protein (HERV-W Env), preferably against HERV-W Envelope protein of the type-W human endogenous retrovirus family (HERV-W), more preferably against the envelope protein of MSRV, more preferably against the extracellular domain the envelope protein of MSRV. Preferably, the antibody of the invention comprises all the 6 CDRs as depicted in SEQ ID No: 1 to 6.

As used herein, the term "biological sample" as used herein refers to any biological sample obtained for the purpose of evaluation in vitro. In the present invention, the sample or patient sample may comprise any body fluid or disease-specific tissue and lesions. Examples of body fluid include blood, serum, plasma, nipple aspirate fluid, urine, saliva, synovial fluid and cerebrospinal fluid (CSF). Examples of disease-specific tissue and lesions include MS brain plaque, CIDP nerve biopsies or diabetes pancreas biopsies.

Antibody for Use as an Antiretroviral Drug

Pathogenic HERV-W expression is occurring in certain individuals when associated with pathological conditions, in particular when expressing Multiple-Sclerosis Associated (MSRV) elements of this HERV-W family. This has been shown to involve the envelope protein as the sole pathogenic player among HERV-W-encoded proteins when exposed to the immune system or to neuroglial cells despite evidence of HERV-W gag-encoded antigens in patients.

To date, the therapeutic strategy has consisted in targeting the HERV-W Envelope protein with a neutralizing humanized antibody, in order to prevent and to inhibit its immunoinflammatory and neuropathogenic effects in HERV-W associated human diseases. Consequently, this therapeutic approach is directed upstream of the inflammatory cascade and of targeted cytotoxic effects, in particular, upstream of the inflammatory demyelinating cascade with remyelination blockade at the origin of lesions with impaired healing potential in MS central nervous system (CNS).

The inventors have evaluated a humanized IgG4 antibody which selectively bond to the extracellular domain of the envelope protein of MSRV, herein called "GNbAC1" for its safety and pharmacokinetics in healthy volunteers in a Phase I clinical trial. This antibody has also been evaluated in MS patients during one year, with repeated infusions of GNbAC1 antibody every 4 weeks at 6 mg/Kg or 2 mg/kg in two parallel cohorts. In the latter Phase IIa clinical trial in MS patients, the inventors have obtained blood samples from Patients before and during the study on which HERV-W biomarkers were tested for the first time after 6 months of treatment by quantitative RT-PCR (qRT-PCR) in order to study the specific HERV-W env and pol mRNAs expression along with treatment by GNbAC1.

The results thereby obtained have revealed a completely unexpected and unknown effect of HERV-W Env protein neutralization in vivo by GNbAC1 antibody.

Indeed, the inventors found out that human patients treated with this antibody have revealed an inhibitory effect on the HERV-W retroviral genome expression itself, which is not limited to the env gene expressing the envelope protein as specifically targeted by GNbAC1. Indeed, the results of the inventors indisputably indicate that both env mRNA (encoding HERV-W Envelope protein) and pol mRNA (encoding HERV-W enzymes, including reverse-transcriptase) levels displayed a parallel and progressive decrease after three and six months of treatment, compared to levels measured before treatment in the same patients.

Thus, a significant anti-retroviral effect on HERV-W expression has been observed after 6 months of treatment with GNbAC1, and affected both env and pol gene expressions in parallel. As retroviral HERV-W RNA expression is not expected to be regulated by HERV-W Envelope protein expression, all the more mRNA from the pol gene that encodes totally unrelated antigenic proteins, the inventors conclude that an unknown effect of HERV-W Env (or MSRV-Env) produces a positive effect on HERV-W genetic regulation relating to its disease-associated expression, as seen in patients with MS, and has been antagonized by GNbAC1 in patients from phase IIa clinical trial carried out by the inventors (see Example 1). This effect is not at all related to known HERV-W Env pathophysiological effects on immune and neuroglial systems.

Consequently, in a first aspect, the invention relates to an antibody, a fragment or a derivative thereof for use as an antiretroviral drug targeting a virus belonging to human endogenous retroviruses (HERV), wherein said antibody, fragment or derivative is directed against HERV-W Envelope protein (HERV-W Env).

As used herein, the expression "antiretroviral drug targeting a virus belonging to human endogenous retroviruses (HERO" refers to an antibody, a fragment or a derivative thereof able to inhibit the expression and/or the replication of a virus belonging to human endogenous retroviruses (HERV). More specifically, said expression refers to an antibody able to:
  suppress or inhibit totally or partially the replication of a virus belonging to the HERV, preferably belonging to the HERV-W family. Typically, said suppression or inhibition of the replication is global and complete; or
  suppress or inhibit totally or partially the expression of a virus belonging to human endogenous retroviruses (HERV), preferably a virus belonging to human endogenous retroviruses type-W (HERV-W) family or the expression of the envelope protein of said virus.

Preferably, said virus belongs to the type-W human endogenous retrovirus family (HERV-W). More preferably, said virus is MSRV. In this specific embodiment, the antibody of the invention is directed against the Envelope protein of MSRV.

In a preferred embodiment, the antiretroviral drug according the invention suppresses or inhibits totally or partially the expression of the env- and/or pot-encoded proteins of a virus belonging to HERV, preferably a virus belonging to HERV-W.

The inventors have shown that targeting the specific envelope protein of MSRV leads to the surprising effect of inhibiting or suppressing the expression of the virus. As previously mentioned, MSRV is implicated in the onset and in the development of several diseases. Consequently, the antibody of the invention is highly promising for use for treating an HERV-W associated disease, preferably a pathology associated with expression of HERV-W Envelope protein (HERV-W Env).

Preferably, said HERV-W associated disease is selected from the group consisting of multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes such as type 1 or type 2 diabetes.

More preferably, said HERV-W associated disease is selected from the group consisting of Multiple Sclerosis (MS) and Chronic Inflammatory Demyelinating Polyneuropathy (CIDP).

In one embodiment, the invention also pertains in an agent for use for preventing and/or treating a disease selected from the group consisting of multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes such as type 1 or type 2 diabetes, wherein said agent consists of an antibody directed against HERV-W Envelope protein (HERV-W Env) or a fragment or derivative thereof. In this specific embodiment, the antibody prevents the HERV-W expression.

In one embodiment, the antibody, fragment or derivative of the invention comprises each of the 6 CDRs as depicted in SEQ ID No: 1, SEQ ID No: 2, SEQ ID No: 3, SEQ ID No: 4, SEQ ID No: 5, and SEQ ID No: 6.

In one embodiment, the antibody, fragment or derivative of the invention comprises:
  a light chain wherein the variable domain comprises each of the 3 CDRs as depicted in SEQ ID No: 1 for CDR-L1, SEQ ID No: 2 for CDR-L2 and SEQ ID No: 3 for CDR-L3; and
  a heavy chain wherein the variable domain comprises each of the 3 CDRs as depicted in SEQ ID No: 4 for CDR-H1, SEQ ID No: 5 for CDR-H2 and SEQ ID No: 6 for CDR-H3.

The above mentioned complementarity determining regions (CDRs) are disclosed in Table 1:

TABLE 1

CDR domains of an antibody according to the invention

| Domains | SEQ ID No: | Sequence |
|---|---|---|
| CDR-L1 | 1 | Ser Ala Ser Ser Ser Val Ser Tyr Met Tyr |
| CDR-L2 | 2 | Arg Thr Ser Asn Leu Ala Ser |
| CDR-L3 | 3 | Gln Gln Tyr Gln Ser Leu Pro Leu Thr |
| CDR-H1 | 4 | Asp Tyr Glu Met His |
| CDR-H2 | 5 | Ala Val Ala Pro Glu Thr Gly Gly Thr Ala Tyr Asn Gln Lys Phe Lys Gly |
| CDR-H3 | 6 | Thr Val Val Pro Phe Ala Tyr |

In one embodiment, the antibody, fragment or derivative of the invention comprises:
  a light chain variable region (VL) as depicted in SEQ ID No: 7; and
  a heavy chain variable region (VH) as depicted in SEQ ID No: 8.

The above mentioned light and heavy variable regions are disclosed in Table 2:

TABLE 2

Light and heavy variable regions of an antibody according to the invention

| Domains | SEQ ID No: | Sequence |
|---|---|---|
| VL | 7 | Gln Ile Gln Leu Thr Gln Ser Pro Ser Ser Leu Ser Ala Ser Val Gly Asp Arg Val Thr Ile Thr Cys Ser Ala Ser Ser Ser Val Ser Tyr Met Tyr Trp Tyr Gln Gln Lys Pro Gly Lys Ala Pro Lys Ala Trp Ile Tyr Arg Thr Ser Asn Leu Ala Ser Gly Val Pro Ser Arg Phe Ser Gly Ser Gly Ser Gly Thr Asp Tyr Thr Leu Thr Ile Ser Ser Leu Gln Pro Glu Asp Phe Ala Thr Tyr Tyr Cys Gln Gln Tyr Gln Ser Leu Pro Leu Thr Phe Gly Gly Gly Thr Lys Val Glu Ile Lys |
| VH | 8 | Gln Val Gln Leu Val Gln Ser Gly Ala Glu Val Lys Lys Pro Gly Ser Ser Val Lys Val Ser Cys Lys Ala Ser Gly Tyr Thr Phe Thr Asp Tyr Glu Met His Trp Val Arg Gln Ala Pro Gly Gln Gly Leu Glu Trp Ile Gly Ala Val Ala Pro Glu Thr Gly Gly Thr Ala Tyr Asn Gln Lys Phe Lys Gly Arg Ala Thr Ile Thr Ala Asp Lys Ser Thr Ser Thr Ala Tyr Met Glu Leu Ser Ser Leu Arg Ser Glu Asp Thr Ala Val Tyr Tyr Cys Thr Ser Thr Val Val Pro Phe Ala Tyr Trp Gly Gln Gly Thr Leu Val Thr Val Ser Ser |

In one embodiment, the antibody, fragment or derivative of the invention is selected from the group consisting of a Fv, Fab, F(ab')2, Fab', dsFv, scFv, sc(Fv)2, a diabody, and multispecific antibodies formed from antibody fragments.

In a preferred embodiment, the antibody of the invention is a monoclonal antibody. Monoclonal antibodies of the invention are monovalent, bivalent, multivalent, monospecific, bispecific, or multispecific. In another embodiment, the antibody directed against HERV-W Env is a binding fragment or a conjugate. For examples antibodies of the invention may be conjugated to a growth inhibitory agent, cytotoxic agent, or a prodrug-activating enzyme.

It may be also desirable to modify the antibody of the invention with respect to effector functions, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992).

Another type of amino acid modification of the antibody of the invention may be useful for altering the original glycosylation pattern of the antibody. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

In another embodiment, the antibody of the invention is a monoclonal humanized antibody, more preferably an IgG4 humanized monoclonal antibody.

Said humanized antibody may be produced by obtaining nucleic acid sequences encoding for CDRs domain by inserting them into an expression vector for animal cell having genes encoding a heavy chain constant region identical to that of a human antibody; and a light chain constant region identical to that of a human antibody, and expressing the expression vector by introducing it into an animal cell. The humanized antibody expression vector may be either of a type in which a gene encoding an antibody heavy chain and a gene encoding an antibody light chain exist on separate vectors or of a type in which both genes exist on the same vector (tandem type). In respect of easiness of construction of a humanized antibody expression vector, easiness of introduction into animal cells, and balance between the expression levels of antibody H and L chains in animal cells, a tandem type of the humanized antibody expression vector is more preferable. Examples of the tandem type humanized antibody expression vector include pKANTEX93, pEE18 and the like. Methods for producing humanized antibodies based on conventional recombinant DNA and gene transfection techniques are well known in the art. Antibodies can be humanized using a variety of techniques known in the art including, for example, CDR-grafting, veneering or resurfacing, and chain shuffling. The general recombinant DNA technology for preparation of such antibodies is also known.

Thus, an embodiment of the invention relates to a monoclonal humanized antibody comprising:
- a light chain wherein the variable domain comprises each of the 3 CDRs as depicted in SEQ ID No: 1 for CDR-L1, SEQ ID No: 2 for CDR-L2 and SEQ ID No: 3 for CDR-L3; and
- a heavy chain wherein the variable domain comprises each of the 3CDRs as depicted in SEQ ID No: 4 for CDR-H1, SEQ ID No: 5 for CDR-H2 and SEQ ID No: 6 for CDR-H3.

In a particular embodiment, the heavy chain (HC) of said humanized antibody has the amino acid sequence as set forth in SEQ ID No: 9 and the light chain (LC) of said antibody has the amino acid sequence set forth in SEQ ID No: 10. This specific antibody is referred to herein as "GNbAC1".

The above mentioned heavy and light chains are disclosed in Table 3:

TABLE 3

HC and LC of the humanized antibody

| Domains | SEQ ID No: | Sequence |
|---|---|---|
| HC | SEQ ID No: 9 | Gln Val Gln Leu Val Gln Ser Gly Ala Glu Val Lys Lys Pro Gly Ser Ser Val Lys Val Ser Cys Lys Ala Ser Gly Tyr Thr Phe Thr Asp Tyr Glu Met His Trp Val Arg Gln Ala Pro Gly Gln Gly Leu Glu Trp Ile Gly Ala Val Ala Pro Glu Thr Gly Gly Thr Ala Tyr Asn Gln Lys Phe Lys Gly Arg Ala Thr Ile Thr Ala Asp Lys Ser Thr Ser Thr Ala Tyr Met Glu Leu Ser Ser Leu Arg Ser Glu Asp Thr Ala Val Tyr Tyr Cys Thr Ser Thr Val Val Pro Phe Ala Tyr Trp Gly Gln Gly Thr Leu Val Thr Val Ser Ser Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Lys Thr Tyr Thr Cys Asn Val Asp His Lys Pro Ser Asn Thr Lys Val Asp Lys Arg Val Glu Ser Lys Tyr Gly Pro Pro Cys Pro Pro Cys Pro Ala Pro Glu Phe Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Gln Glu Gln Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val |

TABLE 3-continued

HC and LC of the humanized antibody

| Domains | SEQ ID No: | Sequence |
|---|---|---|
| | | Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys |
| LC | SEQ ID No: 10 | Gln Ile Gln Leu Thr Gln Ser Pro Ser Ser Leu Ser Ala Ser Val Gly Asp Arg Val Thr Ile Thr Cys Ser Ala Ser Ser Ser Val Ser Tyr Met Tyr Trp Tyr Gln Gln Lys Pro Gly Lys Ala Pro Lys Ala Trp Ile Tyr Arg Thr Ser Asn Leu Ala Ser Gly Val Pro Ser Arg Phe Ser Gly Ser Gly Ser Gly Thr Asp Tyr Thr Leu Thr Ile Ser Ser Leu Gln Pro Glu Asp Phe Ala Thr Tyr Tyr Cys Gln Gln Tyr Gln Ser Leu Pro Leu Thr Phe Gly Gly Gly Thr Lys Val Glu Ile Lys Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys |

Composition for Use as an Antiretroviral Drug

The inventors further investigated the newly unveiled antiretroviral effect of the antibody of the invention. For this purpose, they evaluated its effect in vitro on cell cultures expressing HERV-W gag, pol and env-encoded proteins, as detected by specific antibodies in Western-Blot analysis.

The inventors have confirmed that the expression of the pol protein corresponding to the HERV-W reverse-transcriptase (RT) appeared less important in cells cultured in the presence of GNbAC1, in addition to the decrease in pol RNA levels in patients treated with GNbAC1. Moreover, RT is known to amplify the retroviral expression by generating additional copies of retroviral DNA from expressed RNA. These newly produced retroviral DNA copies can then express corresponding RNA, thereby amplifying the global expression of the retroviral element by multiplying expressing copies through a product of this expression itself, such as RT from pol RNA.

Consequently, they had the idea that the combination of both GNbAC1 and an inhibitor of retroviral reverse-transcriptase such as azidothymidine (AZT) could produce better inhibitory effects on HERV-W expression, in particular on its RT expression as presently exemplified.

This was thus further studied and, quite surprisingly, this combination of an antibody directed against HERV-W Env and of a retroviral reverse-transcriptase inhibitory drug, abolished the expression of HERV-W RT protein in these productive cells.

In parallel and simultaneous cultures, the positive detection of HERV-W RT by Western Blot in untreated cells and the slight or partial reduction in cells treated with GNbAC1 or AZT alone, confirmed the specificity and the significance of this observation: in the same conditions, the combination of both GNbAC1 antibody neutralizing HERV-W Env protein and AZT had abolished the detection of this HERV-W RT protein.

Therefore, in a second aspect, the invention relates to a composition comprising an antibody, a fragment or a derivative according to the invention; and a retroviral reverse-transcriptase inhibitory drug, for use as an antiretroviral drug targeting a virus belonging to human endogenous retroviruses (HERV).

Preferably, said retroviral reverse-transcriptase inhibitory drug is selected from the group consisting of azidothymidine, entecavir, lamivudine, adefovir, sofosbuvir, didanosine, tenofovir, abacavir, lam ivudine, stavudine, emtricitabine, zalcitabine, telbivudine, and didanosine. More preferably, said retroviral reverse-transcriptase inhibitory drug is azidothymidine (AZT). All the previously disclosed technical data are applicable here.

The composition of the invention provides unexpected and novel perspective for therapeutic intervention on HERV-W pathogenic expression. The treatment with a combination of:
an antibody directed against HERV-W Env, such as GNbAC1; and
a molecule targeting reverse-transcriptase itself and/or its activity such as AZT, proved to be highly useful for inhibiting the HERV-W RT expression in diseases associated with HERV-W.

Thus, the invention also pertains to a composition comprising:
an antibody, a fragment or a derivative according to the invention; and
a retroviral reverse-transcriptase inhibitory drug, for use for preventing and/or treating an HERV-W associated disease.

The invention also relates to a composition comprising:
an antibody, a fragment or a derivative according to the invention; and
a retroviral reverse-transcriptase inhibitory drug,
for use for preventing and/or treating a disease selected from the group consisting of multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes such as type 1 or type 2 diabetes. More preferably, said disease is selected from the group consisting of Multiple Sclerosis (MS) and Chronic Inflammatory Demyelinating Polyneuropathy (CIDP).

All the previously disclosed technical data are applicable here.

In a third aspect, the invention relates to an antibody directed against HERV-W Envelope protein (HERV-W Env) or a fragment or derivative thereof, and a retroviral reverse-transcriptase inhibitory drug, preferably azidothymidine as a combined preparation for simultaneous, separate or sequential use in a method for treating an HERV-W associated disease, preferably, a disease selected from the group consisting of multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes such as type 1 or type 2 diabetes.

All the previously disclosed technical data are applicable here.

Kit According to the Invention

The expression of these HERV-W elements in patients with disease and/or their detection in disease-specific tissue and lesions identifies and defines the general category of HERV-W associated diseases or syndromes. It also reflects the biological activity of HERV-W during the time-course of the disease evolution and during its treatments.

Thus, the detection of HERV-W with improved sensitivity, with particular disease specificity or with particular association with clinical features in patients with HERV-W associated diseases or syndromes, constitutes an important value for the diagnostic identification and stratification, as well as for the follow-up and the therapeutic monitoring of the patients. From a panel of primers, probes and PCR protocols, the inventors have thus selected and developed a kit of primers and probes, which revealed useful for detecting the presence and/or measuring the level of expression of HERV in patients.

Consequently, in a fourth aspect, the invention relates to a kit comprising at least one, preferably at least two, preferably at least three, preferably at least four, preferably at least five, preferably at least six, preferably at least seven, preferably at least eight, preferably at least nine, preferably at least ten oligonucleotide selected from the group consisting of SEQ ID No: 11 to 28.

Preferably, said kit comprises at least SEQ ID No: 17 and/or 18 or SEQ ID No: 19, and 20.

Alternatively, said kit comprises:
SEQ ID No: 19, 20, 23, 24 and 25; or
SEQ ID No: 17, 18, 23, 24 and 25; or
SEQ ID No: 19, 20, 14, 15, 16, 23, 24 and 25; or
SEQ ID No: 17, 18, 14, 15, 16, 23, 24 and 25.

More preferably, the kit of the invention comprises all the oligonucleotides as depicted in SEQ ID No: 11 to 28. Typically, said kit is intended to be used for performing a PCR or, more particularly, a quantitative PCR (qPCR) assay. Therefore, the kit preferably also comprises primers and/or probes from reference cellular genes most appropriate for RNA or DNA relative quantification and for various indications.

Said kit preferably further comprises:
SEQ ID No: 26, 27 and 28; or
Sequences specific for GUSB gene; or
Sequences specific for RNAse P gene; or
Sequences specific for a reference cellular gene for relative quantification by qPCR.

Said kit is useful for monitoring the detection and/or the quantification of a virus and belonging to the type W human endogenous retrovirus family (HERV-W), comprising MSRV but also other HERV-W subtype(s). More specifically, the kit of the invention is useful for detecting and/or quantifying the sequences coding for HERV-W Env as those coding for HERV-W pol polyprotein, including RT. Typically, the detection and/or the quantification of HERV-W in a patient encompasses:

(i) the detection and/or the quantification of specific HERV-W RNA, DNA or antigens, preferably detected in body fluids or in disease-specific tissues and lesions, (ii) the detection and/or the quantification of elevated DNA or RNA copy number in cells or tissues from the blood or from organs with lesions or dysfunctions.

Consequently, in a fifth aspect, the invention relates to an antibody directed against HERV-W Envelope protein (HERV-W Env), a fragment or derivative thereof for use as an antiretroviral drug targeting a virus belonging to HERV, preferably to HERV-W, more preferably to MSRV, in a patient suffering from an HERV-W associated disease, wherein said patient is identified by a method comprising a step i) of detecting and/or quantifying HERV-W in a biological sample.

In this specific embodiment, the physician would thereby be able to adapt and optimize appropriate medical care of a patient suffering from an HERV-W associated disease. The monitoring of the presence and/or of the level of expression of HERV-W is highly appropriate for follow-up care and clinical decision making. Indeed, the physician can define the appropriate therapy with optimal strategy for each patient.

Typically, step i) of detection and/or quantification may be performed according to the routine techniques, well known of the person skilled in the art. Typically, said step i) comprises contacting a biological sample of the patient with selective reagents such as probes, primers, ligands or antibodies, and thereby detecting the presence of nucleic acids or proteins of interest originally in the sample. Preferably, said step i) of detecting the presence and/or quantifying HERV-W is performed with the kit according to the invention.

All the previously mentioned technical data are applicable here.

Pharmaceutical Composition

A further object of the invention relates to a pharmaceutical composition comprising an effective dose of an antibody directed against HERV-W Envelope protein (HERV-W Env) and optionally comprising a retroviral reverse-transcriptase inhibitory drug.

Any therapeutic agent of the invention as above described may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody directed against HERV-W Envelope protein (HERV-W Env) may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

Preferably, the antibody directed against HERV-W Envelope protein (HERV-W Env) of the invention or the fragment and the derivative thereof can be formulated into a buffer in which it was solubilized, stored and injected to patients. Preferably, said buffer comprises 20 mM histidine, 5% sucrose, and 0.01% polysorbate 20 and present a pH of 6.0. One example a formulation used for intravenous administration of GNbAC1 is presented in Example 3.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the patient being treated. The person responsible for administration will, in any event, determine the appropriate dose for the individual patient.

In addition to the compounds formulated for parenteral administration, such as intravenous or intramuscular injection, other pharmaceutically acceptable forms include, e.g. tablets or other solids for oral administration; time release capsules; and any other form currently used.

Therapeutic Method and Monitoring Method According to the Invention

The invention also relates to a method for inhibiting the expression and/or the replication of a virus belonging to human endogenous retroviruses (HERV) in a patient by administering to said patient an antibody directed against HERV-W Envelope protein (HERV-W Env).

In a further embodiment, the invention relates to a method for preventing and/or treating a patient suffering from a disease selected from the group consisting of multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes such as type 1 or type 2 diabetes, by administering to said patient an antibody directed against HERV-W Envelope protein (HERV-W Env), a fragment or a derivative thereof, wherein said antibody acts as an antiretroviral drug targeting HERV, preferably targeting HERV-W, more preferably targeting MSRV.

The invention also relates to a method of treatment of a patient suffering from a HERV-W associated disease comprising the steps of:
1) predicting the prognosis of a patient by detecting and/or quantifying a virus belonging to human endogenous retroviruses (HERV) family, preferably HERV-W, more preferably MSRV, in a biological sample by with the kit of the invention; and then
2) if said step 1) shows the expression of a human endogenous retrovirus (HERV), then the method of the invention comprises a step 3) of providing the antibody, fragment or derivative of the invention to said patient.

The invention also relates to a method for monitoring the response to a treatment of a patient suffering from an HERV-W associated disease, said method comprising the following steps:
a. treating said patient with the antibody, fragment or derivative according to the invention; then
b. detection and/or quantification of HERV-W in a biological sample of said patient.

In another embodiment, the invention relates to a method for monitoring the response to a treatment of a patient suffering from an HERV-W associated disease, said method comprising a step of detecting and/or quantifying HERV-W in a biological sample of said patient. Preferably, said patient comprises an antibody, a fragment or a derivative according to the invention. The expression "patient comprising an antibody" refers to a patient who was treated with an antibody and presents a detectable amount of said antibody in his blood, tissues, or organs. Typically, said antibody, fragment or derivative was provided or administered to the patient previously to the step of detecting and/or quantifying HERV-W.

According to the invention, in case of monitoring the response to a treatment of a patient suffering from an HERV-W associated disease, a biological sample may be a sample of body fluids such as blood, cerebrospinal fluid, urine or in a disease-specific tissue and lesions such as MS brain plaques, CIDP nerve biopsies, or diabetes pancreas biopsies.

Typically, step b. of detection and/or quantification may be performed according to the routine techniques, well known of the person skilled in the art. Typically, said step b. comprises contacting a biological sample of the patient with selective reagents such as probes, primers, ligands or antibodies, and thereby detecting the presence of nucleic acids or proteins of interest originally in the sample. Preferably, said step b. of detecting the presence and/or measuring the level of expression of HERV-W is performed with the kit according to the invention.

All the previously disclosed technical feature are applicable here.

FIGURES LEGENDS

Figure 1B:
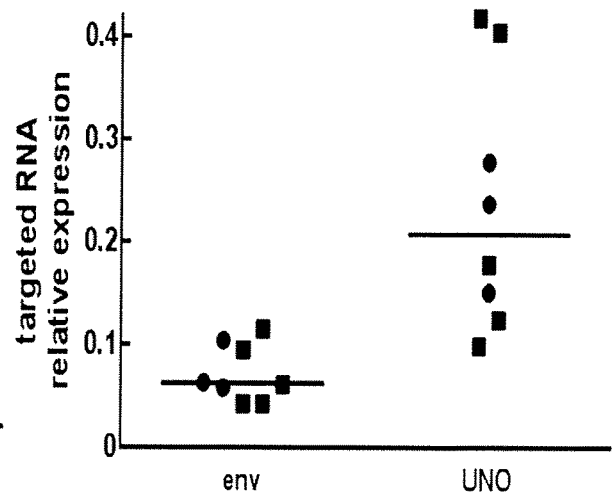
Figure 1C:
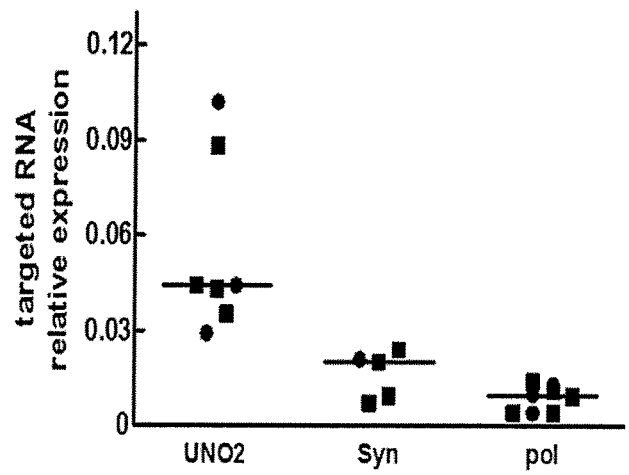
Figure 2A:
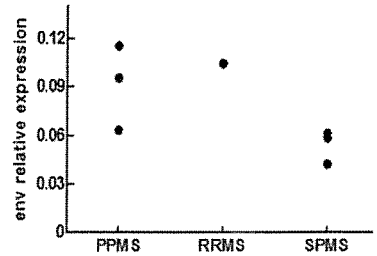
Figure 2B:
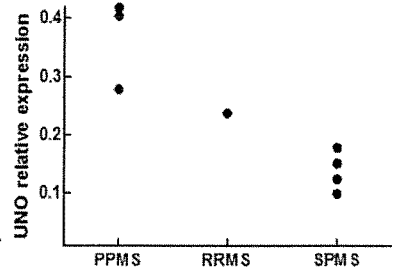
Figure 2C:
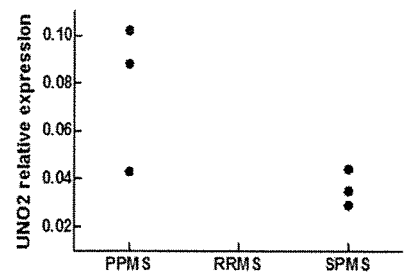
Figure 2D:
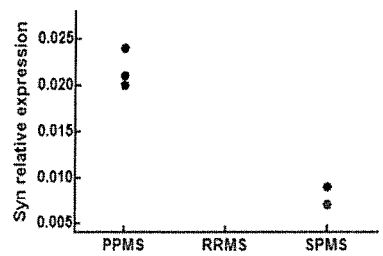
Figure 2E:
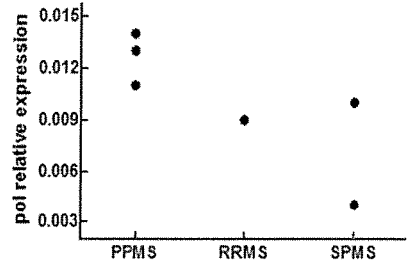

FIG. 1A-C (A) HERV-W env and pol transcript levels at inclusion, as detected by different primer pairs and probes for qPCR.

(B) HERV-W env transcript with "env" and "UNO" primers and probes in parallel for patients included for the 2 mg/ml cohort (plain circles) and for the 6 mg/ml cohort (plain squares).

(C) HERV-W env transcript with "UNO2", "syn" and "pol" primers and probes in parallel for patients included for the 2 mg/ml cohort (plain circles) and for the 6 mg/ml cohort (plain squares).

Ordinates represent the relative expression (ratio to GUS B) of the targeted RNA for each patient and abscises represent the different qPCR protocols used on the same samples.

FIG. 2A-E: Difference in HERV-W env and pol transcript levels between different clinical forms of MS at inclusion, as detected by different primer pairs and probes for qPCR (A) "env" protocol (B) "UNO" protocol (C) "UNO2" protocol (D) "syn" protocol (E) "pol" protocol.

Ordinates represent the relative expression (ratio to GUS B) of the targeted RNA for each patient and abscises represent the different clinical forms of MS: Primary Progressive (PPMS), Relapsing-Remitting (RRMS) and Secondary Progressive (SPMS).

Figure 3A:
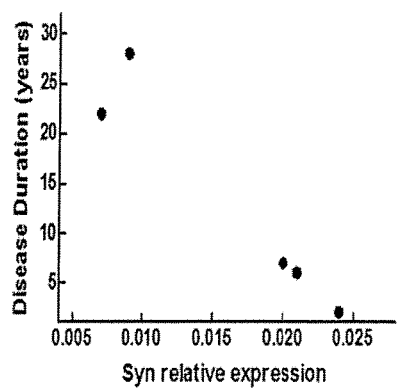
Figure 3B:
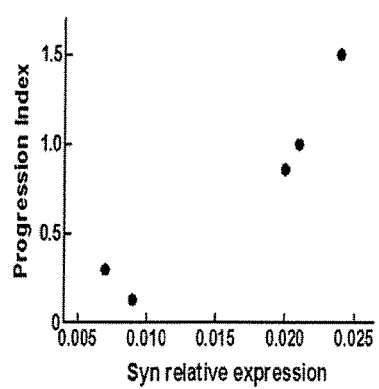
Figure 3C:
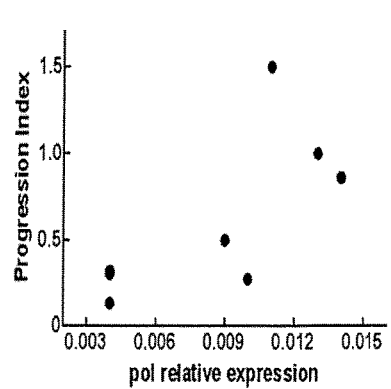

FIG. 3A-C: Correlation between HERV-W env and pol transcript levels and clinical parameters of MS patients at inclusion, as detected by particular primer pairs and probes for qPCR (A) "Syn" protocol evidences a negative correlation between Syncytin-type HERV-W expression and disease duration: Pearson's correlation test r=−0.96; p=0.009 (B) "Syn" protocol evidences a positive correlation between Syncytin-type HERV-W expression and disease progression index: Pearson's correlation test r=0.95; p=0.014 (C) "pol" protocol also evidences a positive correlation between type HERV-W pol gene (encoding the protease, reverse-transcriptase and integrase) expression and disease progression index: Pearson's correlation test r=0.95; p=0.048.

Ordinates represent Disease duration in years (A) or progression index (B & C); abscisses represent the relative expression (ratio to GUS B) of the targeted RNA for each patient.

Figure 4A:
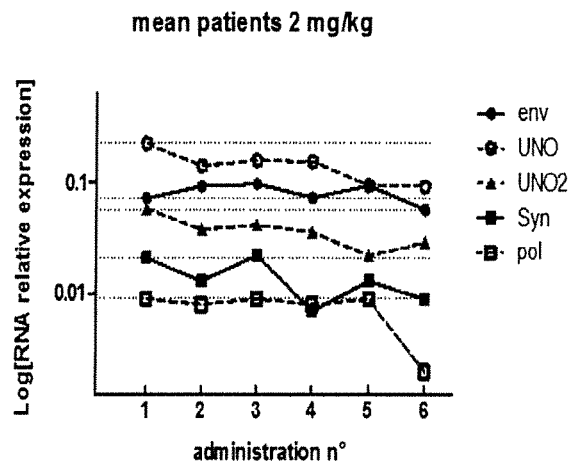
Figure 4B:
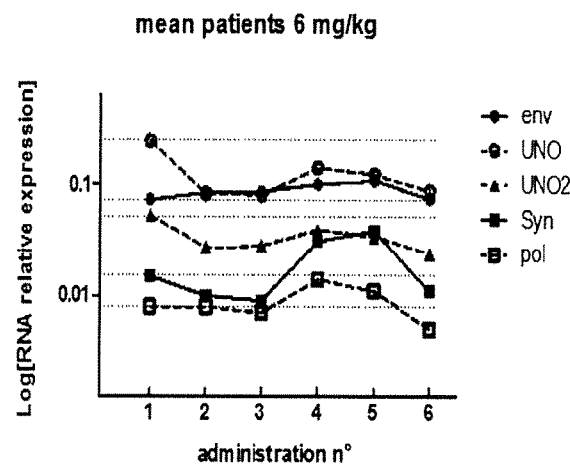
Figure 4C:
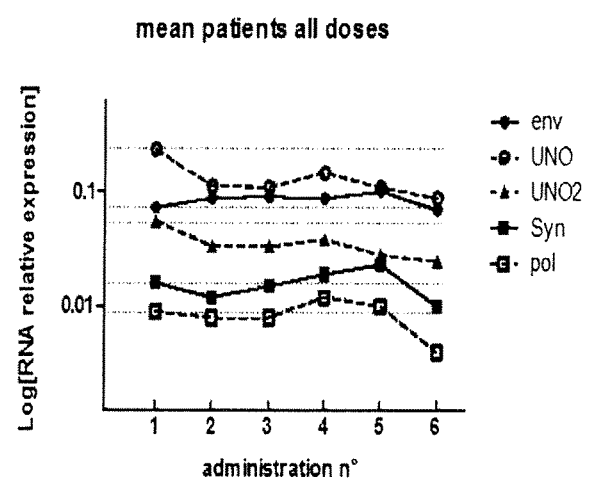
Figure 5A:
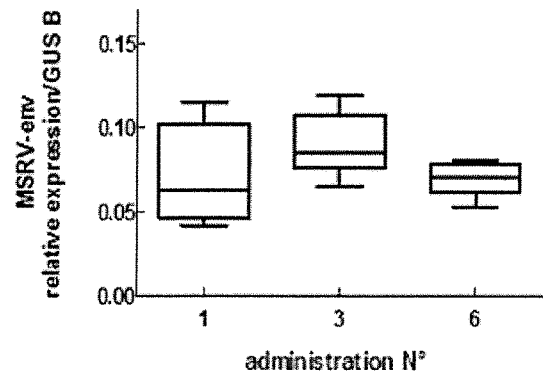
Figure 5B:
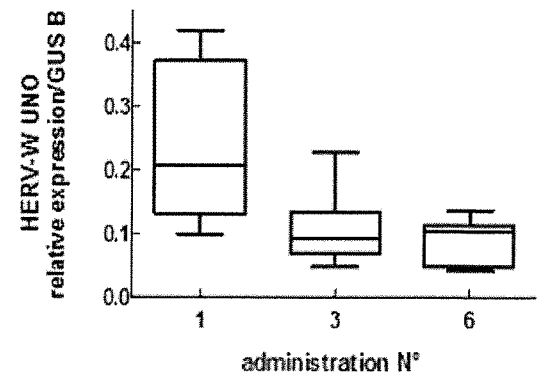
Figure 5C:
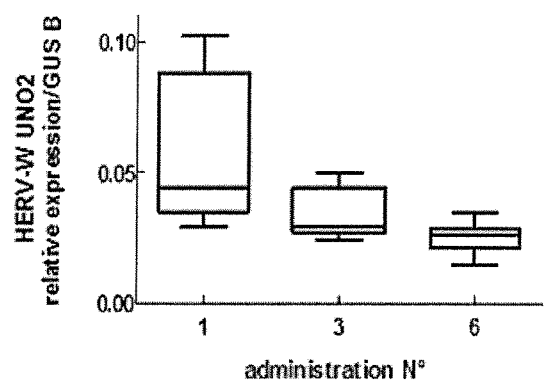
Figure 5D:
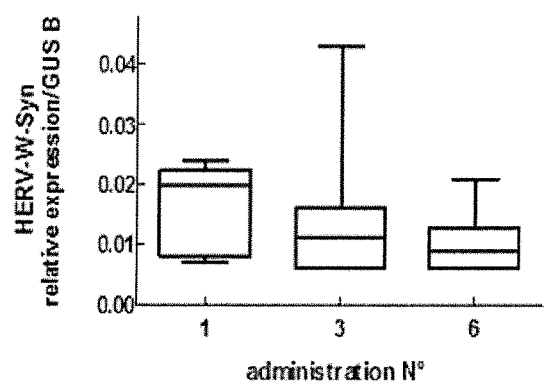
Figure 5E:
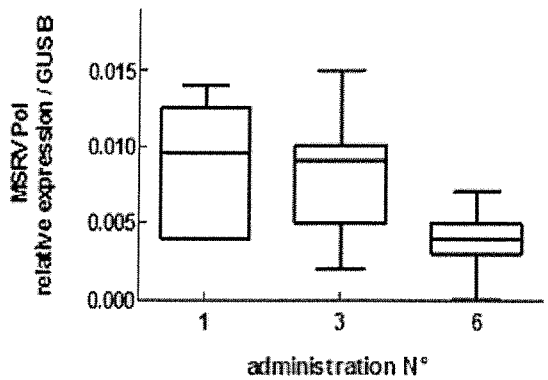

FIG. 4A-C: Variation of HERV-W related transcripts levels during the first 6 months of GNC002. Data represent the mean targeted RNA relative expression to GUS B for each HERV-W related transcripts in the 2 mg/kg cohort (A), in the 6 mg/kg cohort (B), and all patients included in GNC002 (C). Dashed lines represent the level of corresponding transcripts at inclusion. Ordinates represent the average relative expression (ratio to GUS B) of the targeted RNA for each qPCR protocol in the group of patient. Abscises represent the number of injections of GNbAC1 to the patients.

FIG. 5A-E: Variation of HERV-W related transcripts levels during the first 6 months of GNC002. Data represent the mean targeted RNA relative expression to GUS B for each HERV-W transcript in all patients included in GNC002. The variation in HERV-W env and pol transcript levels along with treatment in MS from inclusion to the date of the sixth injection is illustrated, as Whiskers plots (10-90 percentiles) of data from each patient as measured with different primer pairs and probes for qPCR (A) "env" protocol (B) "UNO" protocol (C) "UNO2" protocol (D) "syn" protocol (E) "pol" protocol.

Ordinates represent the average relative expression (ratio to GUS B) of the targeted RNA for each qPCR protocol in the group of patient. Abscises represent the number of injections of GNbAC1 to the patients, before which blood samples were collected (therefore "1" correspond to the status before any injection, "3", the status 4 weeks after the second injection and "6", the status 4 weeks after the fifth injection.

Figure 6:
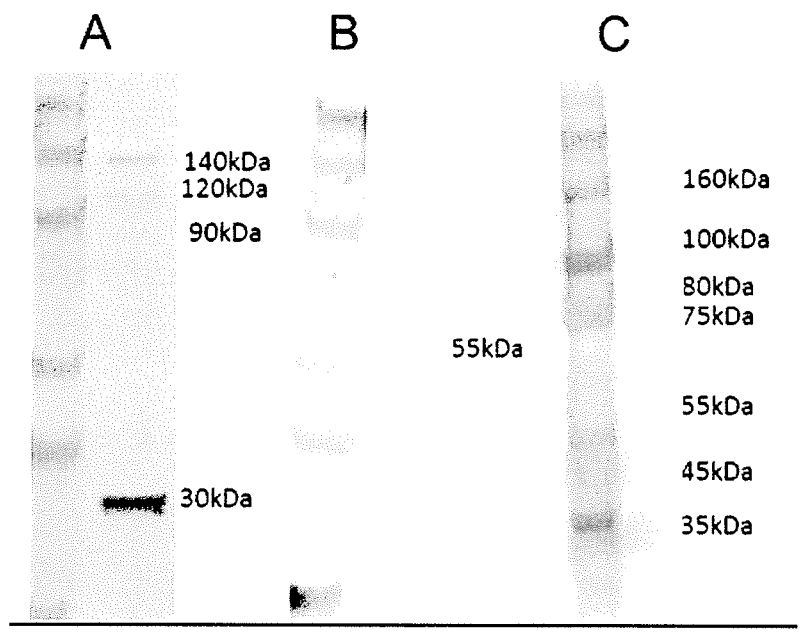

FIG. 6: CH2 cells spontaneously express gag, pol and env-encoded HERV-W proteins, as detected with specific antibody by western blotting.

The apparent molecular weight for bands detected with each specific antibody against HERV-W gag, pol and env-encoded antigens is indicated in the right side of the lane corresponding to the cellular extract for each antigen. The left lane in A, B and C represent the molecular weight markers used for the estimation of KDa.

(A) HERV-W Gag polyprotein and cleavage products, including the typical capsid protein about 30 KDa.
(B) HERV-W Pol polyprotein and cleavage products, including the typical reverse-transcriptase protein about 55 KDa.
(C) HERV-W Envelope protein, cleavage products and multimers, including the SU (surface) and TM (trans-membrane) cleaved units about 45 and 35 KDa. Glycosylated env products are detected with potential variation in glycosylations between monomeric bands detected around 75 and 80 KDa. The 55 KDa corresponds to the no-glycosylated monomer, with a dimer around 100 KDa. The band around 160 KDa could be either a glycosylated dimer or a non-glycosylated trimer FIG. 7: HERV-W pol-encoded Reverse-Transcriptase protein in CH2 cultures with or without treatment by GNbAC1 and/or AZT.

The apparent molecular weight for detected bands with the specific antibody against HERV-W pol-encoded antigens is indicated in the right side of the Western Blot. The number of the western-blot lanes (1 to 6) are indicated below the picture.

1) Combined treatment with GNbAC1 and AZT
2) Treatment with AZT only
3) Treatment with GNbAC1 only
4) Mock-treated cells (no treatment)
5) Empty well
6) Molecular weight marker

EXAMPLES

Example 1: Inhibition of Human Endogenous Retrovirus Type W mRNA Expression in Patients with Multiple Sclerosis Treated with GNbAC1

GNbAc1 is an IgG4 monoclonal antibody directed toward the multiple sclerosis associated retrovirus envelope protein (MSRV-Env), a member of the HERV-W family of endogenous retroviral elements, therefore also referred to as HERV-W Env. GNbAC1 has shown a favorable safety profile and linear pharmacokinetics in a Phase 1 clinical trial conducted in healthy volunteers.

The present GNC002 Phase IIa clinical trial was performed to assess the safety profile and the pharmacokinetics of GNbAC1 at 2 and 6 mg/kg in 10 MS patients. GNC002 consisted in a 12 months longitudinal study, in which GNbAC1 is administered on a monthly basis.

The present analysis was conducted on samples collected during the first 6 months of GNC002, where HERV-W related transcripts levels were assessed by real time quantitative polymerase chain reaction (RT-qPCR) in peripheral blood mononuclear cells (PBMC) of enrolled patients. HERV-W transcripts are assessed by different primers/probe sets as follows: MSRV-env, HERV-W-UNO, HERV-W-UNO2, Materials and Methods Samples were collected in 4 ml CPT Vacutainer tubes, processed, stored and shipped according to the protocol provided by Geneuro in the GNC002 Laboratory Manual.

Frozen PBMC from 10 MS patients were provided by the 2 recruiting centers involved in the GNC002 study.

Chemicals and Biological Material

| Item | Supplier | Reference | Lot n° |
|---|---|---|---|
| 2-β-mercaptoethanol | Sigma | M3148-100 ml | 18596EK |
| DNA Zap 1 | Ambion | AM9891G | 1108021 |
| DNA Zap 2 | Ambion | AM9892G | 1108017 |
| Ethanol | Fluka | 51976-500 ml | BCBH0821V |
| IQ supermix | Biorad | 1708862 | 730001658 |
| IQ supermix with SYBR green | Biorad | 170-8882 | 730001695 |
| i-script select cDNA synthesis kit | Biorad | 1708897 | 730001741 |
| Nuclease free water | Ambion | AM9932 | 1303123 |
| PBS pH 7.4 10X | Ambion | AM9625 | 1305040 |
| QIAshredder (250) | Qiagen | 79656 | 139309935 |
| Rneasy mini kit (250) | Qiagen | 74106 | 139314102 |
| Turbo DNA-free kit | Ambion | AM1907 | 1303051 |

Softwares
  Biorad CFX Manager 2.0: PCR execution and analyses
  Genex 5: smoothing of PCR raw data
  Graph Pad Prism: plots
  SigmaStat: statistical analyses
The Normality test used is the Kolmogorov-Smirnov test. Correlations were determined with the Pearson Product Moment analysis if data were parametric, or the Spearman Rank Order analysis if data were non-parametric.

Protocols

Briefly, the first step consisted in the extraction of total RNA from PBMC samples. Samples were PBMC isolated from blood collected on CPT tubes and frozen in 0.5 ml of DMSO 10% in Foetal Calf Serum. After thawing, PBMC samples were washed with ice-cold PBS and total RNAs were extracted with QIAamp RNeasy Mini Kit. Then, cDNAs were prepared by retro-transcribing all mRNA contained in previously extracted total RNAs. Quantitative PCRs were conducted on these cDNAs, with addition of an internal standard used as an inter-plate calibrator (allowing the standardization of the values throughout an experiment with multiple plates). Results were expressed as the relative expression of the targeted RNA (MSRV/HERV-W), by a ratio to the expression of GUS B RNA, a reference housekeeping gene with a stable expression level in MS population.

Primers and Probe Sequences

The commercial detection primers/probe set for the control housekeeping gene, GUS B, is the Taqman Gene Expression Assay GusB (Applied biosystem 4448485). VIC® is the fluorescent dye label detected at the 5'-end of the GusB probe.

MSRV-env primers and probe are designed to specifically detect the sequence coding for MSRV-Env protein and not Syncytin. Conversely, Syncytin primers allow the specific amplification of sequence coding for Syncytin, but not MSRV-env. The fluorescence of FAM™ dye label is measured on MSRV-env and Syncytin probe.

UNO2 primers are designed by Geneuro to recognize the sequence of MSRV-Env supposed to have potential immuno-suppressive function, by analogy with corresponding region in other endogenous retrovirus sequences; nonetheless this terminology ("immunosuppressive peptide/sequence") is used here to locate a defined domain in retroviral envelope proteins, which may not be immunosuppressive at all in many retroviruses. These primers can hybridize the sequence coding for Syncytin too.

UNO, designed by Geneuro_bind sequences coding for MSRV-Env and Syncytin. No probe is designed for the sequences amplified by UNO and UNO2 primers, thus SYBR green fluorescence allows the quantification of the amplification of these sequences.

MSRV-pol primers and probe were designed by Geneuro and recognize the sequence coding for the MSRV reverse transcriptase. The detection of MSRV-pol probe hybridization is quantified with FAM™ fluorescent reporter.

TABLE 4

Sequence of all primers and probe used in this biomarker study

| TARGET: | PRIMERS DESIGNATION | SEQUENCE (5'→3') | SEQ ID NO: |
|---|---|---|---|
| Multiple sclerosis retrovirus Env | MSRVenv Fwd | 5'-CTTCCAGAATTGAAGCTGTAAAGC-3' | 11 |
| | MSRVenv Rev | 5'-GGGTTGTGCAGTTGAGATTTCC-3' | 12 |
| | MSRVenv Probe | FAM-TTCTTCAAATGGAGCCCCAGATGCAG-TAMRA | 13 |
| Syncytin-1 | Syncytin M fwd | 5'-ACTTTGTCTCTTCCAGAATC-3' | 14 |
| | Syncytin M rev | 5'-GCGGTAGATCTTAGTCTTGG-3' | 15 |
| | Syncytin M probe | FAM-ATGGAGCCCAAGATGCA-TAMRA | 16 |
| Potential immuno-suppressive sequence | UNO2 fwd | 5'-GGCGGTTAGCAAGTCTAAAG-3' | 17 |
| | UNO2 rev | 5'-ATGGAACAGGTCACTGACTCC-3' | 18 |

TABLE 4-continued

Sequence of all primers and probe used in this biomarker study

| TARGET: | PRIMERS DESIGNATION | SEQUENCE (5'→3') | SEQ ID NO: |
|---|---|---|---|
| Both Syncytin and MSRV-env sequences | UNO fwd | 5'-GTATGTCTGATGGGGGTGGAG-3' | 19 |
| | UNO rev | 5'-CTAGTCCTTTGTAGGGGCTAGAG-3' | 20 |
| | Syncytin fwd | 5'-TGCCCCATCGTATAGGAGTCT-3' | 21 |
| | Syncytin rev | 5'-CATGTACCCGGGTGAGTTGG-3' | 22 |
| MSRV-pol sequence (reverse transcriptase) | MSRVpol2 fwd | 5'-CCTGTACGTCCTGACTCTC-3' | 23 |
| | MSRVpol2 rev | 5'-CTTGGGCTAATGCCTGGCC-3' | 24 |
| | MSRV-pol probe 2 | FAM-CCAACGTCTCAACTCACCTGG-TAMRA | 25 |
| GAPDH | GAPDH fwd | 5'-GGTGTGAACCATGAGAAGTATGAC-3' | 26 |
| | GAPDH rev | 5'-TGGCATGGACTGTGGTCATG-3' | 27 |
| | GAPDH probe | VIC-AGCCTCAAGATCATCAGCAATGCCTCC-TAMRA | 28 |

The fluorophore detected by CFX thermocycler is in 5' of the probe. For the primers set without probe the detection is performed with intercalating SYBR green dye.

Analyses of Results

Exclusion Criteria for Samples Preventing Biases in the Analyses were as Follows:

RNA concentration of the sample below 10 ng/μL, after extraction and DNase treatment Standard deviation of the PCR triplicate above 0.2 Cq, for one sample Cq (Cycle of Quantification) of GUS B above the degradation cut-off, which indicates that the RNA is not reaching the expected quality level in the study. The degradation cut-off is calculated as follows: Mean+2× Standard Deviation of all individual GUS B Cq values All individual Cq for MSRV/HERV-W env genes and GUS B are standardized according to their own internal standards added on each experimental plate with Genex® software (MultiD analyses AB, Sweden).

The Relative Expression of each targeted RNA within each sample is calculated as follows:

Targeted RNA Relative Expression to GUS $B = 2^{(Cq\ GUS\ B - Cq\ targeted\ RNA)}$ Extraction Yields and Samples Exclusion After extraction, the total RNA concentration for each sample is determined with a Nanodrop® apparatus. All samples with total RNA concentration below 10 ng/μl were excluded. Before total RNA quantification, total RNA underwent a DNase treatment to eliminate contaminating genomic DNA eventually remaining in the total RNA preparation.

After this DNase step, the absence of contaminating genomic DNA for each sample was controlled by a PCR without retrotranscription (NoRT Ctrl no 1). If genomic DNA is detected during this step, corresponding samples underwent a second DNase step, and a second RNA quantification, as well as a second NoRT control (NoRT Ctrl no 2). Samples were finally excluded if genomic DNA was still present in the preparation, or if total RNA was below 10 ng/μl after this additional DNase treatment.

Standardizing Raw Data with Genex® and Exclusion of Samples

In order to harmonize raw data collected through multiple PCR microplates, all raw data were standardized according to the internal standard present on each microplate with Genex software. Samples for which the standard deviation of the PCR triplicate was above 0.2 Cq were excluded from the study. The quality of a sample is reflected by its GUS B expression level. All samples above the degradation cut-off were excluded from the study.

Results

HERV-W Related Transcripts Levels at Inclusion

At the first time point of the study, PBMCs were isolated from the blood of all subjects before the first administration of GNbAC1 or placebo. Thus, the results presented in Table 5 and in FIG. 1 correspond to the basal level of HERV-W related transcripts of interest for each patient at the time of inclusion in the study.

TABLE 5

HERV-W related transcripts levels at inclusion.

| | | | Relative expression targeted RNA to GUS B | | | | |
|---|---|---|---|---|---|---|---|
| Sample | Timepoint | Dose (mg/kg) | Relative expression MSRV-env/GusB | Relative expression UNO/GusB | Relative expression UNO2/GusB | Relative expression Syncytin/GusB | Relative expression MSRV-pol/GusB |
| 01-0001 12 | 1 | 2 | | | | | |
| 01-0003 12 | 1 | 2 | 0.058 | 0.151 | 0.044 | | 0.010 |
| 01-0004 12 | 1 | 2 | | | | | |
| 02-0002 12 | 1 | 2 | 0.042 | 0.099 | 0.029 | | 0.004 |
| 02-0005 12 | 1 | 2 | 0.115 | 0.418 | 0.102 | 0.021 | 0.013 |
| 01-0006 12 | 1 | 6 | 0.104 | 0.237 | | | 0.009 |
| 01-0008 12 | 1 | 6 | 0.063 | 0.278 | 0.043 | 0.024 | 0.011 |
| 02-0007 12 | 1 | 6 | 0.061 | 0.178 | 0.044 | 0.009 | 0.004 |
| 02-0009 12 | 1 | 6 | 0.042 | 0.124 | 0.035 | 0.007 | 0.004 |
| 02-0010 12 | 1 | 6 | 0.095 | 0.404 | 0.088 | 0.020 | 0.014 |

The distribution of results from all patients is homogeneous with "env" and "syn" qPCR protocols but differences in distribution can be seen with UNO and UNO2 protocols despite lower relative expression detected for RNA specifically targeted with "UNO2".

No difference in HERV-W transcripts levels distribution at inclusion was observed between patients being enrolled in the 2 mg/kg and the 6 mg/kg cohorts and between both recruiting centres involved in the study.

Comparison of HERV-W Env and Pol Transcript Levels with Clinical Data at Inclusion The correlation of clinical parameters with HERV-W related transcripts levels at inclusion was evaluated according to the information summarized in table 6.

toring. This can also be useful for stratifying disease "duration versus activity" in progressive MS with "Syn" qPCR, raising perspectives for differences in therapeutic strategies to be applied according to the HERV-W env "Syncytin" transcriptional level in patients with progressive evolution over several years (SPMS, in particular).

HERV-W Related Transcripts Levels Over 6 Months

For each patient included in the study, PBMCs were isolated from blood sample at Day 1 (inclusion), Day 2, Day 8, Day 15, and Day 29. Afterwards, patients have received 5 additional monthly GNbAC1 administrations and PBMCs were isolated from blood sample before each infusion of

TABLE 6

HERV-W related transcripts levels and clinical information at inclusion

| | | | Relative expression targeted RNA to GUS B | | | | | Clinical Information | | | | |
|---|---|---|---|---|---|---|---|---|---|---|---|---|
| Sample | Time-point | Dose (mg/kg) | Relative expression MSRV-env/GusB | Relative expression UNO/GusB | Relative expression UNO2/GusB | Relative expression Syncytin/GusB | Relative expression MSRV-pol/GusB | Age | Diagnostic | Disease Duration | EDSS at inclusion | Progression Index |
| 01-0001 12 | 1 | 2 | | | | | | | | | | |
| 01-0003 12 | 1 | 2 | 0.058 | 0.151 | 0.044 | | 0.010 | 49 | spms | 22 | 6 | 0.27 |
| 01-0004 12 | 1 | 2 | | | | | | | | | | |
| 02-0002 12 | 1 | 2 | 0.042 | 0.099 | 0.029 | | 0.004 | 52 | spms | 14 | 4.5 | 0.32 |
| 02-0005 12 | 1 | 2 | 0.115 | 0.418 | 0.102 | 0.021 | 0.013 | 59 | ppms | 6 | 6 | 1 |
| 01-0006 12 | 1 | 6 | 0.104 | 0.237 | | | 0.009 | 57 | rrms | 5 | 2.5 | 0.5 |
| 01-0008 12 | 1 | 6 | 0.063 | 0.278 | 0.043 | 0.024 | 0.011 | 51 | ppms | 2 | 3 | 1.5 |
| 02-0007 12 | 1 | 6 | 0.061 | 0.178 | 0.044 | 0.009 | 0.004 | 62 | spms | 28 | 3.5 | 0.13 |
| 02-0009 12 | 1 | 6 | 0.042 | 0.124 | 0.035 | 0.007 | 0.004 | 47 | spms | 22 | 6.5 | 0.3 |
| 02-0010 12 | 1 | 6 | 0.095 | 0.404 | 0.088 | 0.020 | 0.014 | 65 | ppms | 7 | 6 | 0.86 |

Firstly, these results evidenced the fact that, whatever the primers and probes used for the different qPCR protocols and whatever the HERV-W genes (env or pol), the highest HERV-W RNA levels were found in PPMS patients and the lowest in SPMS patients (FIG. 2). This clearly provided new information of interest on the differential HERV-W transcriptional expression level in patients with two different forms of Progressive MS (PPMS and SPMS). This may also be of interest for RRMS but only one such case is represented here with intermediate relative expression.

This shows that the quantification of HERV-W transcriptional level in MS patients can have a diagnostic value and can, e.g., be used for the purpose of supporting a differential diagnosis between SPMS and PPMS cases. This can also be useful for stratifying qPCR thresholds for prognosis or therapeutic monitoring in PPMS, SPMS and, eventually also, in RRMS.

Secondly, despite presently low numbers, statistically significant correlations were found between HERV-W env and pol RNA transcriptional levels and the disease duration and/or the progression index, when using the "Syn" and "pol" protocols. The other protocols using different primers and probes did not yield significant correlations with clinical parameters, which highlights the value of the selected protocol, as shown in FIG. 3.

This shows that a selection of protocols for the quantification of HERV-W transcriptional level of the env gene encoding the Syncytin subtype ("Syn" protocol, with SEQ ID No: 14, 15 and 16) or the pol gene in general ("pol" protocol, with SEQ ID No: 23, 24 and 25) can also have a particular diagnostic value in MS. Here, "syn" and "pol" qPCR protocol can be used as a biomarker of HERV-W related disease activity (evolutivity of disease progression) for clinical stratification, follow-up and therapeutic monitoring.

antibody. Thus, the following results represent the variation of each HERV-W related transcript over the first 6 months of GNC002 study.

The second GNbAC1 administration occurred at different time points from Day 1, depending on patients. Thus, the mean variation of HERV-W related transcripts was assessed with blood samples collected before each GNbAC1 administration only.

In the 2 mg/kg cohort, a decrease of all HERV-W transcript levels was observed at the 6$^{th}$ GNbAC1 administration, when compared to basal values at inclusion (FIG. 4). This is confirmed in the 6 mg/kg cohort (FIG. 4). When all patients (2 mg/kg and 6 mg/kg cohorts) are grouped, the decrease is better evidenced by HERV-W UNO, UNO2, and pol qPCR protocols throughout the GNC002 study (FIG. 4). This is also illustrated with statistical distribution of values measured before the first, third and sixth GNbAC1 injection in all patients (FIG. 5).

Very unexpectedly, the decrease is also marked for pol mRNA. This effect is not what an antibody specifically binding to HERV-W Env protein is expected to produce after being injected once a month over six months in patients with a disease-associated HERV-W expression. This effect on mRNAs encoding reverse-transcriptase, protease and integrase enzymes therefore appears unique and novel for an anti-Env antibody such as GNbAC1. It therefore evidences an effect on the global HERV-W expression itself and, through its pol encoded products, on its replicative retroviral activity. Therefore it shows an anti-retroviral effect, in particular an anti-endogenous retrovirus effect targeting the HERV-W family.

In FIG. 5, the selection of the most accurate primers and probes for qPCR protocols for a therapeutic monitoring of patient groups treated with GNbAC1 or with any drug interfering with HERV-W expression, is "UNO2" for HERV-W env and "pol" for HERV-W enzymes encoding pol gene. Nonetheless, calculation of ratios with figures obtained by other qPCR protocols can also reveal of diagnostic or prognostic interest.

In this experiment, HERV-W related transcripts levels in MS patients included in GNC002 study were assessed by real time quantitative PCR, using different sets of primers amplifying different HERV-W env gene representative sequences and one set of primers amplifying the HERV-W pol sequences (within Reverse-transcriptase coding region). HERV-W transcripts investigated here are denominated MSRV-env, HERV-W-UNO, HERV-W-UNO2, HERV-W-Syn and MSRV-pol.

The results clearly indicate that these biomarkers can provide sensitive bioclinical data of interest for diagnosis of MS and for the therapeutic monitoring of HERV-W associated diseases.

Furthermore, HERV-W related transcripts levels seem to be higher in PPMS than in SPMS patients, which confirms the value of the present quantitative PCR tests with the different sets of primers for bioclinical evaluation of patients and, beyond, for differential diagnosis purposes between MS progressive forms (SPMS and PPMS).

Since all HERV-W related transcripts levels decreased over the first 6 months of GNC002 in both 2 mg/kg and 6 mg/kg cohorts, this confirms the bioclinical value of the present sets of primers and qPCR protocols for the therapeutic monitoring of the patients and for a bioclinical evaluation of therapeutic efficiency.

Finally, this also provides biological evidence that anti-HERV-W Env antibody treatment (such as GNbAC1) in patients with MS has an inhibitory effect on HERV-W expression, which was not expected for env mRNA level, but even less for pol mRNA. This clearly indicates an efficacy of this anti-Env antibody treatment against an endogenous retrovirus associated with a human disease, as has never been described with human exogenous retroviruses.

Example 2: Inhibition of Human Endogenous Retrovirus Type W Pol-Gene Encoded Protein (Reverse-Transcriptase) is Synergistically Enhanced by a Combined Treatment with GNbAC1 Antibody and AZT A. Antigenic Characterization of a Cell Culture Spontaneously Expressing HERV-W Gag, Pol and Env Proteins
Material and Methods
Cell Culture Spontaneously Expressing HERV-W Gag, Pol and Env Proteins Human CH2 cells were maintained in IMDM medium (Ser. No. 12/440,053; Lifetech) supplemented with 10% fetal calf serum (Ser. No. 10/270,106; Invitrogen), 1% penicillin/streptomycin (P4333; Sigma) at 37° C. with 5% CO2. Protein extraction
Protein Extraction CH2 cells were resuspended in 500 µl of RIPA buffer (R0278, SIGMA) containing cOmplete® anti-phosphatase inhibitor cocktail (04 693 132001; Roche) and 0.05% LPG (326495-22-1; Avanti Polar) at 4° C., incubated for 2 hours at 26° C. on a rotating platform and centrifuged at 10000 g for 20 minutes at 26° C. Supernatant were collected and stored at −20° C.
Western Blotting Protein extracts were diluted in 2× Laemmli buffer (Biorad) and heated for 5 minutes at 100° C. before loading. Proteins were separated by 7.5% sodium dodecyl sulfate-polyacrylamide gel electrophoresis (TGX, Biorad). Gels were run for a time period of 15 min at 120 mA in running buffer (Life Technologies). After the protein transfer onto a 0.2 µm nitrocellulose membrane (Biorad), the membrane was washed twice with 1×PBS (Biomerieux) containing 0.05% Tween20 buffer (Sigma) and was blocked for 1 hour with Starting Block (Thermo) on a rotating platform at room temperature. Primary antibodies were used according to Table 1 in 1×PBS for 1 hour. The membrane was then washed three times and incubated for 30 minutes with the HRP-conjugated goat anti-rabbit (G21234; lifetech, 1/1000 in 1×PBS) or mouse (115-035-146; jackson, 1/1000 in 1×PBS) IgG antibody). Protein of interest was detected with a colometric reaction (Opti 4-CN, Biorad), according to the provided protocol.

Antibodies with Targeted antigen and Antibody dilution: 1) Rabbit polyclonal pAb1 (SQ09AK001, Squarix), MSRV-Env, 0.5 µg/ml; 2) Rabbit polyclonal 330110 J77 Serum (330110 J77, InCellArt), MSRV-Pol polyprotein, 1/500; Murine monoclonal 38E12 (250510, Squarix); MSRV-Gag polyprotein, 1 µg/ml.
Results As can be seen from FIG. 6, these cells express all HERV-W structural proteins, as detected by specific antibodies directed against gag, pol and env-encoded proteins.

Of note, anti-gag antibody detects the HERV-W gag-encoded polyprotein and different cleaved proteins, including a stronger detection of the capsid P30-like protein band. The pattern detected by anti-Env antibody appears more complex with detection of HERV-W env-encoded glycosylated and non-glycosylated monomers, dimers and trimers, as well as cleaved SU or TM unit around 45 and 35 KDa. The anti-pol antibody mainly detects the cleaved reverse-transcriptase enzyme, though a high molecular weight band can be seen in the upper part of the gel (not labelled with KDa estimation), which would correspond to the uncleaved HERV-W pol-encoded polyprotein.

B. Human Endogenous Retrovirus Type W Pol-Gene Encoded Protein (Reverse-Transcriptase) can No Longer be Detected in Cells Exposed to a Combined Treatment with GNbAC1 Antibody and AZT
Material and Methods
Chordomas Cell Culture Human CH1 and CH2 cells (1:1) cells were co-cultured for optimizing the growth of CH2 cells and maintained in 6-well plates (CC7672-7506; CytoOne) at a density of $1.10^6$ cell/well in IMDM medium (Ser. No. 12/440,053; Lifetech) supplemented with 10% fetal calf serum (Ser. No. 10/270, 106; Invitrogen), 1% penicillin/streptomycin (P4333; Sigma) at 37° C. with 5% CO2. Cells were treated with i) AZT (1 µg/ml, A21-69; Sigma), ii) GNbAC1 (300 µg/ml, T950111-A; Polymun), iii) AZT+GNbAC1 or corresponding controls with GNbAC1 buffer [20 mM His, 5% Sucrose (w/v), 0.01% Tween 20 (w/v)].
Protein Extraction CH1 and CH2 cells were resuspended in 200 µl of RIPA buffer (R0278, SIGMA) containing cOmplete® anti-phosphatase inhibitor cocktail (04 693 132001; Roche) and 0.05% LPG (326495-22-1; Avanti Polar) at 4° C., incubated for 2 hours at 26° C. on a rotating platform and centrifuged at 10000 g for 20 minutes at 26° C. Supernatant were collected and stored at −20° C.
Western Blotting Protein extracts were diluted (2:1) in 2× Laemmli buffer (Biorad) and heated for 5 minutes at 100° C. before loading. Proteins were separated by 7.5% sodium dodecyl sulfate-polyacrylamide gel electrophoresis (TGX, Biorad). Gels were run for a time period of 15 min at 120 mA in running buffer (Life Technologies). After the protein transfer onto a 0.2 μm nitrocellulose membrane (Biorad), the membrane was washed twice with 1×PBS (Biomérieux) containing 0.05% Tween20 buffer (Sigma) and was blocked for 1 hour with Starting Block (Thermo) on a rotating platform at room temperature. Primary antibodies were used according to Table 1 in 1×PBS for 1 hour. The membrane was then washed three times and incubated for 30 minutes with the HRP-conjugated goat anti-rabbit (G21234; lifetech, 1/400 in 1×PBS) or mouse (115-035-146; jackson, 1/1000 in 1×PBS) IgG antibody). Protein of interest was detected with a colometric reaction (Opti 4-CN, Biorad), according to the provided protocol. Antibody: Rabbit polyclonal 330110 J77 Serum (330110 J77, InCellArt), raised against MSRV-Pol polyprotein and diluted 1/500.

Figure 7:
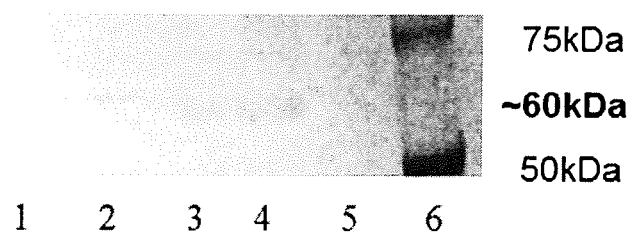

As can be seen from the results of this experiment, which are illustrated in FIG. 7, the cells cultured in presence of the combination of both GNbAC1 and AZT (lane no 1) no longer express detectable levels of HERV-W Reverse-transcriptase (RT). When exposed to AZT alone (Lane no 2) a clear reduction of the HERV-W RT expression is shown by the reduced corresponding signal stained by the anti-HERV-W RT antibody; nonetheless, this remains a partial effect. In lane no 3, the exposure to GNbAC1 alone appeared to have minor effects on HERV-W pol-encode reverse-transcriptase protein, as detected in the present in vitro conditions. As a parallel positive control, the expression of the HERV-W RT protein from cells exposed to the GNbAC1 diluent only (dilution buffer) as a Mock-treatment, show the normal presence of this RT band expressed in these cells in lane no 4.

Thus, it is here shown that only the combination of both GNbAC1 anti HERV-W Env antibody and Azidothymidine (AZT) had sufficient effect to completely inhibit HERV-W RT production from this culture of human cells expressing HERV-W gag, pol and env genes altogether, whereas each therapeutic molecule alone had only partial or very little effect on this HERV-W expression. Even if this relates to in vitro cell culture conditions, this nonetheless evidences an obviously increased and a major synergistic effect on the efficacy of the inhibition of HERV-W RT expression by this unique combination of an antibody neutralizing HERV-W Env protein and of an anti-retroviral reverse-transcriptase drug. These therapeutic molecules are not expected to synergize effects on RT expression of an endogenous retrovirus such as HERV-W, all the more because (i) they specifically target completely different molecules and protein structures, (ii) they have completely different modes of action (Env neutralization by specific epitope targeting and inhibition of RT enzyme activity) and (iii) one is an antibody while the other is a small chemical molecule.

Example 3: Formulation of a Buffer Solution for GNbAC1 Antibody Preparation Suitable for Intravenous Injection in Human Individuals As mentioned in example 1, GNbAc1 is an IgG4 monoclonal antibody directed toward the multiple sclerosis associated retrovirus envelope protein (MSRV-Env), a member of the HERV-W family of endogenous retroviral elements, therefore also referred to as HERV-W Env. GNbAC1 has shown a favourable safety profile and linear pharmacokinetics in a Phase clinical trial conducted in healthy volunteers. The GNC002 Phase IIa clinical trial was performed to assess the safety profile and the pharmacokinetics of GNbAC1 at 2 and 6 mg/kg in 10 MS patients. GNC002 consisted in a 12 months longitudinal study, in which GNbAC1 is administered on a monthly basis.

For the purpose of intravenous (iv) administration of the GNbAC1 antibody, a specifically suitable formulation of the buffer in which it was solubilized, stored and injected to patients, is the following: 20 mM histidine, 5% sucrose, 0.01% polysorbate 20, pH 6.0.

The invention claimed is:

1. A method for inhibiting the expression and/or the replication of a virus belonging to a type W human endogenous retroviruses (HERV-W) in a patient, comprising administering to said patient a combined preparation comprising:

an antibody or a fragment thereof, directed against HERV-W Envelope protein (HERV-W Env), wherein said antibody or fragment comprises each of the 6 CDRs as depicted in SEQ ID No: 1, SEQ ID No: 2, SEQ ID No: 3, SEQ ID No: 4, SEQ ID No: 5 and SEQ ID No: 6; and a retroviral reverse-transcriptase inhibitory drug.

2. The method according to claim 1, wherein said antibody or fragment and said retroviral reverse-transcriptase inhibitory drug are administered simultaneously, separately or sequentially to the patient.

3. The method according to claim 1, wherein said retroviral reverse-transcriptase inhibitory drug is azidothymidine (AZT).

4. The method according to claim 1, wherein said virus belongs to the MSRV subtype of human endogenous retrovirus family (HERV-W).

5. The method according to claim 4, wherein said virus is MSRV.

6. The method according to claim 1, wherein said antibody or fragment is selected from the group consisting of a Fv, Fab, F(ab')2, Fab', dsFv, scFv, sc(Fv)2, a diabody, and multispecific antibodies formed from antibody fragments.

7. The method according to claim 1, wherein said antibody is a monoclonal humanized antibody.

8. The method according to claim 1, wherein said antibody or fragment comprises:
   a heavy chain (HC) having the amino acid sequence as set forth in SEQ ID No: 9 and
   a light chain (LC) having the amino acid sequence set forth in SEQ ID No: 10.

9. A method for treating an HERV-W associated disease comprising administering to a patient in need thereof a combined preparation comprising:
   an antibody or a fragment thereof, directed against HERV-W Envelope protein (HERV-W Env), wherein said antibody or fragment comprises each of the 6 CDRs as depicted in SEQ ID No: 1, SEQ ID No: 2, SEQ ID No: 3, SEQ ID No: 4, SEQ ID No: 5 and SEQ ID No: 6; and
   a retroviral reverse-transcriptase inhibitory drug,
said HERV-W associated disease being selected from the group consisting of multiple sclerosis (MS), schizophrenia (SZ), bipolar disorder (BP), unipolar or psychotic depression, clinically isolated syndrome (CIS, with neurological symptom), chronic inflammatory demyelinating polyneuropathy (CIDP), epilepsy, psoriasis, cancer, inflammatory pancreatitis and diabetes.

10. The method according to claim 9, wherein the HERV-W associated disease is Multiple Sclerosis (MS) or Chronic Inflammatory Demyelinating Polyneuropathy (CIDP).

11. The method according to claim 9, wherein said antibody or fragment and said retroviral reverse-transcriptase inhibitory drug are administered simultaneously, separately or sequentially to the patient.

12. The method according to claim 9, wherein said retroviral reverse-transcriptase inhibitory drug is azidothymidine (AZT).

13. The method according to claim 9, wherein said virus belongs to the MSRV subtype of human endogenous retrovirus family (HERV-W).

14. The method according to claim 9, wherein said virus is MSRV.

15. The method according to claim 9, wherein said antibody or fragment is selected from the group consisting of a Fv, Fab, F(ab')2, Fab', dsFv, scFv, sc(Fv)2, a diabody, and multispecific antibodies formed from antibody fragments.

16. The method according to claim 9, wherein said antibody is a monoclonal humanized antibody.

17. The method according to claim 9, wherein said antibody or fragment comprises:
   a heavy chain (HC) having the amino acid sequence as set forth in SEQ ID No: 9 and
   a light chain (LC) having the amino acid sequence set forth in SEQ ID No: 10.

18. A method for inhibiting the expression and/or the replication of a virus belonging to a type W human endogenous retroviruses (HERV-W) in a patient, comprising administering to said patient a combined preparation consisting of:
   an antibody or a fragment thereof, directed against HERV-W Envelope protein (HERV-W Env), wherein said antibody or fragment comprises each of the 6 CDRs as depicted in SEQ ID No: 1, SEQ ID No: 2, SEQ ID No: 3, SEQ ID No: 4, SEQ ID No: 5 and SEQ ID No: 6; and
   a retroviral reverse-transcriptase inhibitory drug.

\* \* \* \* \*